(12) United States Patent
Heidmann et al.

(10) Patent No.: US 11,059,803 B2
(45) Date of Patent: Jul. 13, 2021

(54) CRYSTALLINE FORM OF N-[1-(5-CYANO-PYRIDIN-2- YLMETHYL)-1H-PYRAZOL-3-YL]-2-[4-(1-TRIFLUOROMETHYL-CYCLOPROPYL)-PHENYL]-ACETAMIDE

(71) Applicant: IDORSIA PHARMACEUTICALS LTD, Allschwil (CH)

(72) Inventors: Bibia Heidmann, Allschwil (CH); Markus Von Raumer, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 9 days.

(21) Appl. No.: 16/628,618

(22) PCT Filed: Jul. 4, 2018

(86) PCT No.: PCT/EP2018/068087
§ 371 (c)(1),
(2) Date: Jan. 3, 2020

(87) PCT Pub. No.: WO2019/008034
PCT Pub. Date: Jan. 10, 2019

(65) Prior Publication Data
US 2020/0165221 A1 May 28, 2020

(30) Foreign Application Priority Data
Jul. 5, 2017 (WO) ................ PCT/EP2017/066806

(51) Int. Cl.
*C07D 401/06* (2006.01)

(52) U.S. Cl.
CPC ........ *C07D 401/06* (2013.01); *C07B 2200/13* (2013.01)

(58) Field of Classification Search
CPC ........................ C07D 401/06; C07B 2200/13
See application file for complete search history.

(56) References Cited

U.S. PATENT DOCUMENTS

| | | | |
|---|---|---|---|
| 9,932,314 B2 | 4/2018 | Siegrist et al. | |
| 10,065,929 B2 | 9/2018 | Siegrist et al. | |
| 10,246,426 B2 | 4/2019 | Bezencon et al. | |
| 2017/0096399 A1* | 4/2017 | Siegrist | C07D 405/12 |
| 2018/0105496 A1 | 4/2018 | Siegrist et al. | |
| 2018/0230109 A1 | 8/2018 | Bezencon et al. | |
| 2019/0375702 A1 | 12/2019 | McLaren et al. | |

FOREIGN PATENT DOCUMENTS

| WO | WO 2015/186056 | 12/2015 |
|---|---|---|
| WO | WO 2016/041892 | 3/2016 |
| WO | WO 2018/109152 | 6/2018 |
| WO | WO 2018/141961 | 8/2018 |

OTHER PUBLICATIONS

"Remington: The Science and Practice of Pharmacy", 21st Edition, 5 pages (2005).
Berg, A.T. et al, "Revised terminology and concepts for organization of seizures and epilepsies: Report of the ILAE Commission on Classification and Terminology, 2005-2009" *Epilepsia*, vol. 51(4):676-685 (2010).
Griesser, U.J, "The Importance of Solvates" *Polymorphism in the Pharmaceutical Industry*, Chapter 8, 19 pages (2006).

* cited by examiner

*Primary Examiner* — Timothy R Rozof
(74) *Attorney, Agent, or Firm* — Hoxie & Associates LLC

(57) ABSTRACT

The present invention relates to crystalline forms of N-[1-(5-cyano-pyridin-2-ylmethyl)-1H-pyrazol-3-yl]-2-[4-(1-trifluoromethyl-cyclopropyl)-phenyl]-acetamide, pharmaceutical compositions comprising said crystalline forms and their use as T-type calcium channel blockers in the treatment or prevention of diseases or disorders where T-type calcium channels are involved.

12 Claims, 2 Drawing Sheets

CRYSTALLINE FORM OF N-[1-(5-CYANO-PYRIDIN-2- YLMETHYL)-1H-PYRAZOL-3-YL]-2-[4-(1-TRIFLUOROMETHYL-CYCLOPROPYL)-PHENYL]-ACETAMIDE

CROSS REFERENCE TO RELATED APPLICATIONS

This application is a United States Application under 35 U.S.C. 371 claiming benefit of PCT Application No. PCT/EP2018/068087, filed on Jul. 4, 2018, which claims the benefit of PCT Application No. PCT/EP2017/066806, filed on Jul. 5, 2017, the contents of which are incorporated herein by reference.

The present invention relates to crystalline forms of N-[1-(5-cyano-pyridin-2-ylmethyl)-1H-pyrazol-3-yl]-2-[4-(1-trifluoromethyl-cyclopropyl)-phenyl]-acetamide (hereinafter also referred to as "COMPOUND"), pharmaceutical compositions comprising said crystalline forms and their use as T-type calcium channel blockers in the treatment or prevention of diseases or disorders where T-type calcium channels are involved, notably in the treatment or prevention of epilepsy; sleep disorders; sleep disturbances; pain; neurological disorders selected from essential tremors, Parkinson's disease, schizophrenia, depression, anxiety, psychosis, neurodegenerative disorders, autism and drug addiction; cardiovascular disorders selected from hypertension, cardiac arrhythmias, atrial fibrillation, congenital heart failure and heart block; cancer; diabetes; or diabetic neuropathy.

COMPOUND and its activity as T-type calcium channel blocker have been previously described in WO 2015/186056.

Figure 1:
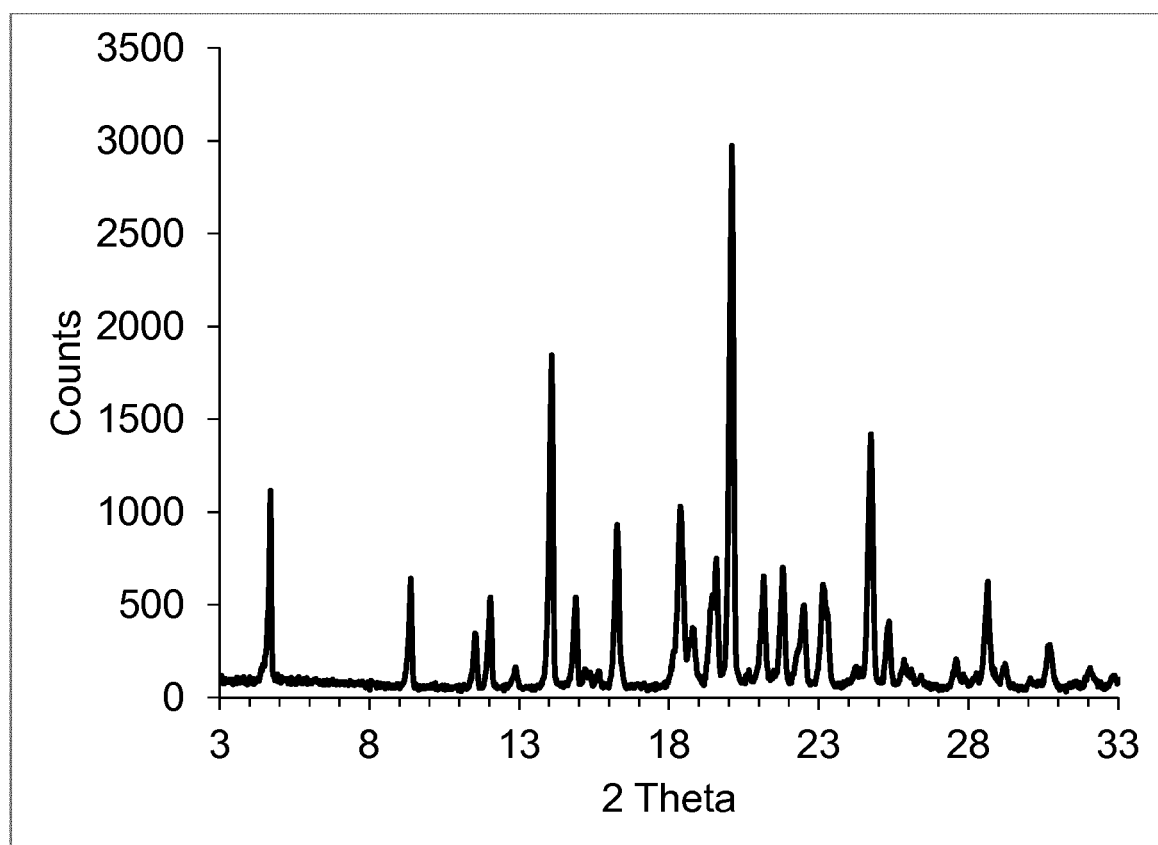
FIG. 1 shows the X-ray powder diffraction diagram of COMPOUND in the crystalline form 1, wherein the X-ray powder diffraction diagram is displayed against Cu Kα radiation. The X-ray diffraction diagram shows peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger or equal than 10% are reported): 4.7° (26%), 9.3° (17%), 12.0° (17%), 14.1° (60%), 16.3° (32%), 18.4° (36%), 20.1° (100%), 21.8° (22%), 24.7° (49%), and 28.6° (21%).
Figure 2:
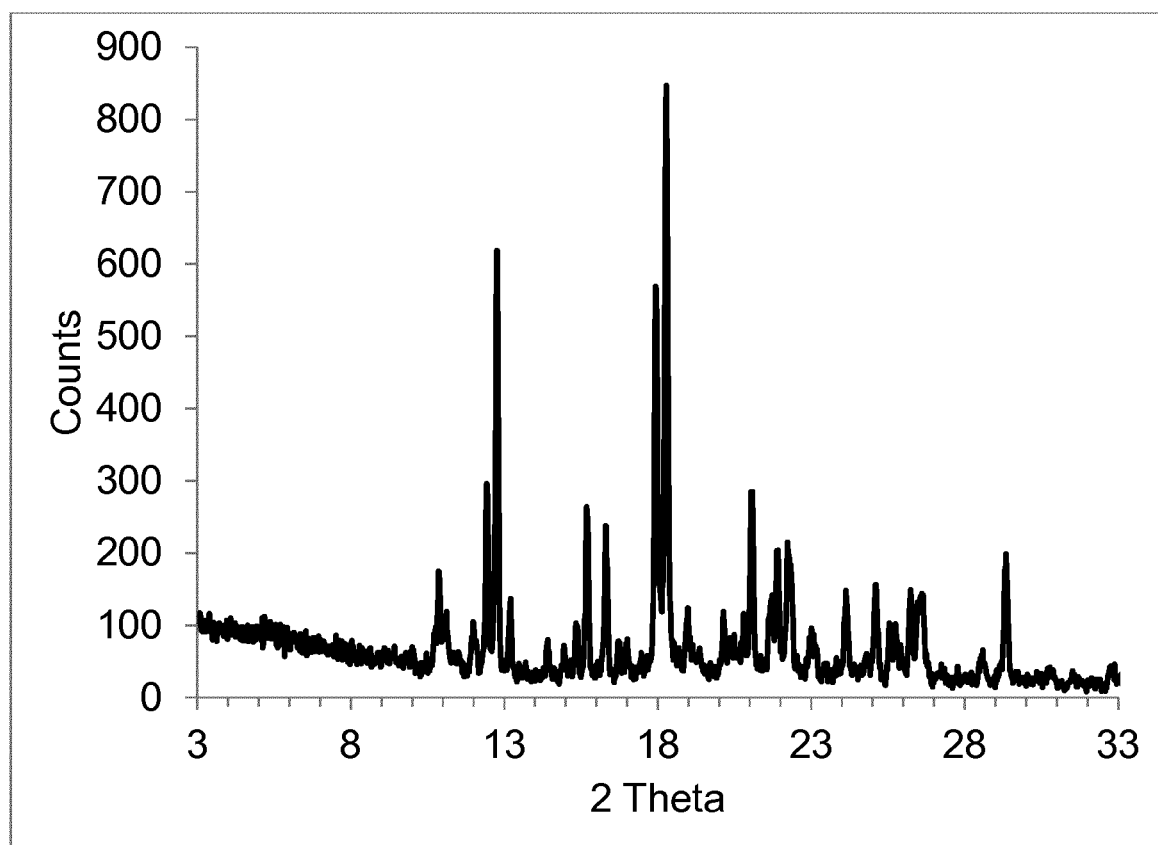
FIG. 2 shows the X-ray powder diffraction diagram of COMPOUND in the crystalline form 2, wherein the X-ray powder diffraction diagram is displayed against Cu Kα radiation. The X-ray diffraction diagram shows peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger or equal than 10% are reported): 10.9° (17%), 12.4° (32%), 12.8° (71%), 13.2° (12%), 15.7° (28%), 16.3° (25%), 18.0° (65%), 18.3° (100%), 21.1° (30%), and 29.3° (21%).

In the X-ray diffraction diagrams of FIG. 1 and FIG. 2 the angle of refraction 2theta (2θ) is plotted on the horizontal axis and the counts on the vertical axis.

For avoidance of any doubt, the above-listed peaks describe the experimental results of the X-ray powder diffraction shown in FIGS. 1 and 2. It is understood that, in contrast to the above peak list, only a selection of characteristic peaks is required to fully and unambiguously characterize COMPOUND in the respective crystalline form of the present invention.

DETAILED DESCRIPTION OF THE INVENTION

1) A first embodiment of the invention relates to crystalline forms of N-[1-(5-cyano-pyridin-2-ylmethyl)-1H-pyrazol-3-yl]-2-[4-(1-trifluoromethyl-cyclopropyl)-phenyl]-acetamide (COMPOUND), characterized by:
   a. the presence of peaks in the X-ray powder diffraction diagram at the following angles of refraction 2θ: 4.7°, 14.1°, and 20.1° (form 1); or
   b. the presence of peaks in the X-ray powder diffraction diagram at the following angles of refraction 2θ: 12.8°, 18.0°, and 18.3° (form 2).

It is understood, that the crystalline forms according to embodiment 1) comprise COMPOUND in a crystalline form of the free base (i.e. not in form of a salt). Furthermore, said crystalline forms may comprise non-coordinated and/or coordinated solvent. Coordinated solvent is used herein as term for a crystalline solvate. Likewise, non-coordinated solvent is used herein as term for physiosorbed or physically entrapped solvent (definitions according to Polymorphism in the Pharmaceutical Industry (Ed. R. Hilfiker, V C H, 2006), Chapter 8: U. J. Griesser: The Importance of Solvates). Both crystalline forms (crystalline form 1 and crystalline form 2) comprise no coordinated water, but may comprise non-coordinated water or another non-coordinated solvent.

COMPOUND in the crystalline form 1 has a melting point of T=147±2° C. as measured by DSC. COMPOUND in crystalline form 1 is not hygroscopic according to Ph. Eur.

2) Another embodiment relates to crystalline forms of COMPOUND according to embodiment 1), characterized by
   a. the presence of peaks in the X-ray powder diffraction diagram at the following angles of refraction 2θ: 4.7°, 9.3°, 14.1°, 20.1°, and 24.7° (form 1); or
   b. the presence of peaks in the X-ray powder diffraction diagram at the following angles of refraction 2θ: 12.4°, 12.8°, 15.7°, 18.0°, and 18.3° (form 2).

3) Another embodiment relates to crystalline forms of COMPOUND according to embodiment 1), characterized by
   a. the presence of peaks in the X-ray powder diffraction diagram at the following angles of refraction 2θ: 4.7°, 9.3°, 12.0°, 14.1°, 16.3°, 18.4°, 20.1°, 21.8°, 24.7°, and 28.6° (form 1); or
   b. the presence of peaks in the X-ray powder diffraction diagram at the following angles of refraction 2θ: 10.9°, 12.4°, 12.8°, 13.2°, 15.7°, 16.3°, 18.0°, 18.3°, 21.1°, and 29.3° (form 2).

4) Another embodiment relates to a crystalline form of COMPOUND according to embodiment 1), characterized by the presence of peaks in the X-ray powder diffraction diagram at the following angles of refraction 2θ: 4.7°, 14.1°, and 20.1°.

5) Another embodiment relates to a crystalline form of COMPOUND according to embodiment 1), characterized by the presence of peaks in the X-ray powder diffraction diagram at the following angles of refraction 2θ: 4.7°, 9.3°, 14.1°, 20.1°, and 24.7°.

6) Another embodiment relates to a crystalline form of COMPOUND according to embodiment 1), characterized by the presence of peaks in the X-ray powder diffraction diagram at the following angles of refraction 2θ: 4.7°, 9.3°, 12.0°, 14.1°, 16.3°, 18.4°, 20.1°, 21.8°, 24.7°, and 28.6°.

7) Another embodiment relates to a crystalline form of COMPOUND according to embodiment 1), which essentially shows the X-ray powder diffraction pattern as depicted in FIG. 1.

8) Another embodiment relates to a crystalline form of COMPOUND according to embodiment 1), characterized by the presence of peaks in the X-ray powder diffraction diagram at the following angles of refraction 2θ: 12.8°, 18.0°, and 18.3°.

9) Another embodiment relates to a crystalline form of COMPOUND according to embodiment 1), characterized by the presence of peaks in the X-ray powder diffraction diagram at the following angles of refraction 2θ: 12.4°, 12.8°, 15.7°, 18.0°, and 18.3°.

10) Another embodiment relates to a crystalline form of COMPOUND according to embodiment 1), characterized by the presence of peaks in the X-ray powder diffraction diagram at the following angles of refraction 2θ: 10.9°, 12.4°, 12.8°, 13.2°, 15.7°, 16.3°, 18.0°, 18.3°, 21.1°, and 29.3°.

11) Another embodiment relates to a crystalline form of COMPOUND according to embodiment 1), which essentially shows the X-ray powder diffraction pattern as depicted in FIG. 2.

12) Another embodiment relates to a crystalline form, such as an essentially pure crystalline form, of N-[1-(5-cyano-pyridin-2-ylmethyl)-1H-pyrazol-3-yl]-2-[4-(1-trifluoromethyl-cyclopropyl)-phenyl]-acetamide (COMPOUND) obtainable by:
   a. heating a suspension comprising N-[1-(5-cyano-pyridin-2-ylmethyl)-1H-pyrazol-3-yl]-2-[4-(1-trifluoromethyl-cyclopropyl)-phenyl]-acetamide in about 5 vol. toluene at reflux until dissolution;
   b. cooling of the solution to about 25° C. within 1 to 5 hours;
   c. cooling to 0° C.; and
   d. isolating of the obtained solid residue.

The isolation step may be performed by any method known in the art to separate a solid precipitate from a liquid, preferably by filtration. After isolation, the solid residue may be optionally washed with a hydrocarbon such as n-pentane, n-hexane, n-heptane or methylcyclohexane (notably n-heptane).

The above process is a recrystallization of COMPOUND. It is thus understood that a "suspension comprising N-[1-(5-cyano-pyridin-2-ylmethyl)-1H-pyrazol-3-yl]-2-[4-(1-trifluoromethyl-cyclopropyl)-phenyl]-acetamide" refers to a suspension containing N-[1-(5-cyano-pyridin-2-ylmethyl)-1H-pyrazol-3-yl]-2-[4-(1-trifluoromethyl-cyclopropyl)-phenyl]-acetamide and various amounts of impurities; the amount of impurities is preferably less than 30% by weight of the amount of COMPOUND (more preferably less than 15% and most preferably less than 3%).

13) Another embodiment relates to a crystalline form of COMPOUND according to embodiment 12), characterized by the presence of peaks in the X-ray powder diffraction diagram at the following angles of refraction 2θ: 4.7°, 14.1°, and 20.1°.

14) Another embodiment relates to a crystalline form of COMPOUND according to embodiment 12), characterized by the presence of peaks in the X-ray powder diffraction diagram at the following angles of refraction 2θ: 4.7°, 9.3°, 14.1°, 20.1°, and 24.7°.

15) Another embodiment relates to a crystalline form of COMPOUND according to embodiment 12), characterized by the presence of peaks in the X-ray powder diffraction diagram at the following angles of refraction 2θ: 4.7°, 9.3°, 12.0°, 14.1°, 16.3°, 18.4°, 20.1°, 21.8°, 24.7°, and 28.6°.

16) Another embodiment relates to a crystalline form of COMPOUND according to embodiment 12), which essentially shows the X-ray powder diffraction pattern as depicted in FIG. 1.

17) Another embodiment relates to the crystalline form of COMPOUND according to any one of embodiments 4) to 7), obtainable by the process of embodiment 12).

18) Another embodiment relates to a crystalline form, such as an essentially pure crystalline form, of N-[1-(5-cyano-pyridin-2-ylmethyl)-1H-pyrazol-3-yl]-2-[4-(1-trifluoromethyl-cyclopropyl)-phenyl]-acetamide (COMPOUND) obtainable by:
   a) dissolution of COMPOUND in about 8 to 10 vol. $(C_{3-6})$alkanone (notably acetone or butanone); and
   b) evaporation of the solvent at ambient conditions.

Preferably the dissolution is done in a glass vial in a small scale of about 4 to 10 mg of COMPOUND. The evaporation is preferably done in an open glass vial.

19) Another embodiment relates to a crystalline form of COMPOUND according to embodiment 18), characterized by the presence of peaks in the X-ray powder diffraction diagram at the following angles of refraction 2θ: 12.8°, 18.0°, and 18.3°.

20) Another embodiment relates to a crystalline form of COMPOUND according to embodiment 18), characterized by the presence of peaks in the X-ray powder diffraction diagram at the following angles of refraction 2θ: 12.4°, 12.8°, 15.7°, 18.0°, and 18.3°.

21) Another embodiment relates to a crystalline form of COMPOUND according to embodiment 18), characterized by the presence of peaks in the X-ray powder diffraction diagram at the following angles of refraction 2θ: 10.9°, 12.4°, 12.8°, 13.2°, 15.7°, 16.3°, 18.0°, 18.3°, 21.1°, and 29.3°.

22) Another embodiment relates to a crystalline form of COMPOUND according to embodiment 18), which essentially shows the X-ray powder diffraction pattern as depicted in FIG. 2.

23) Another embodiment relates to the crystalline form of COMPOUND according to any one of embodiments 8) to 11), obtainable by the processes of embodiment 18).

Based on the dependencies of the different embodiments 1) to 23) as disclosed hereinabove, the following embodiments are thus possible and intended and herewith specifically disclosed in individualised form:

1, 2+1, 3+1, 4+1, 5+1, 6+1, 7+1, 8+1, 9+1, 10+1, 11+1, 12, 13+12, 14+12, 15+12, 16+12, 17+4+1, 17+5+1, 17+6+1, 17+7+1, 18, 19+18, 20+18, 21+18, 22+18, 23+8+1, 23+9+1, 23+10+1, 23+11+1;

in the list above the numbers refer to the embodiments according to their numbering provided hereinabove whereas "+" indicates the dependency from another embodiment. The different individualised embodiments are separated by commas. In other words, "17+4+1" for example refers to embodiment 17) depending on embodiment 4), depending on embodiment 1), i.e. embodiment "17+4+1" corresponds to embodiment 1) further characterised by the features of the embodiments 4) and 17).

For avoidance of any doubt, whenever one of the above embodiments refers to "peaks in the X-ray powder diffraction diagram at the following angles of refraction 2θ", said X-ray powder diffraction diagram is obtained by using combined Cu Kα1 and Kα2 radiation, without Kα2 stripping; and it should be understood that the accuracy of the 2θ values as provided herein is in the range of +/−0.1-0.2°.

Notably, when specifying an angle of refraction 2theta (2θ) for a peak in the invention embodiments and the claims, the 2θ value given is to be understood as an interval from said value minus 0.2° to said value plus 0.2° (2θ+/−0.2°); and preferably from said value minus 0.1° to said value plus 0.1° (2θ+/−0.1°).

Where the plural form is used for compounds, solids, pharmaceutical compositions, diseases and the like, this is intended to mean also a single compound, solid, pharmaceutical composition, disease or the like.

Definitions provided herein are intended to apply uniformly to the subject matter as defined in any one of embodiments 1) to 23), and, mutatis mutandis, throughout the description and the claims unless an otherwise expressly set out definition provides a broader or narrower definition. It is well understood that a definition or preferred definition of a term or expression defines and may replace the respective term or expression independently of (and in combination with) any definition or preferred definition of any or all other terms or expressions as defined herein.

The term "$(C_{3-6})$alkanone" refers to an alkane group containing three to six carbon atoms in which one methylene group "—$CH_2$—" has been replaced by a carbonyl group "—C(O)—". Examples of $(C_{3-6})$alkanone groups are propanone (acetone), butanone, 3-methyl-butan-2-one, 3,3-dimethyl-butan-2-one, pentan-2-one, 3-methyl-pentan-2-one, 4-methyl-pentan-2-one, pentan-3-one, 2-methyl-pentan-3-one, hexan-2-one and hexan-3-one. Preferred are propanone (acetone) and butanone.

The term "essentially pure" is understood in the context of the present invention to mean especially that at least 90, preferably at least 95, and most preferably at least 99 percent by weight of the crystals of COMPOUND are present in a crystalline form according to the present invention.

When defining the presence of peak in e.g. an X-ray powder diffraction diagram, a common approach is to do this in terms of the S/N ratio (S=signal, N=noise). According to this definition, when stating that a peak has to be present in a X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

In the context with stating that the crystalline form essentially shows an X-ray powder diffraction pattern as depicted in FIG. 1 or 2, respectively, the term "essentially" means that at least the major peaks of the diagram depicted in said figures, i.e. those having a relative intensity of more than 20%, especially more than 10%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects. Notably, crystals of COMPOUND in the crystalline form 1 were obtained in form of plates, hence XRPD analysis is prone to orientation effects that may result in missing peaks or intensity variations of single peaks.

Unless used regarding temperatures, the term "about" placed before a numerical value "X" refers in the current application to an interval extending from X minus 10% of X to X plus 10% of X, and preferably to an interval extending from X minus 5% of X to X plus 5% of X; most preferred is X. In the particular case of temperatures, the term "about" placed before a temperature "Y" refers in the current application to an interval extending from the temperature Y minus 10° C. to Y plus 10° C., preferably to an interval extending from Y minus 5° C. to Y plus 5° C. Room temperature means a temperature of about 25° C.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

The crystalline forms, especially the essentially pure crystalline forms, of COMPOUND according to any one of embodiments 1) to 23) can be used as medicaments, e.g. in the form of pharmaceutical compositions for enteral (such especially oral) or parenteral (including topical application or inhalation) administration.

24) Another embodiment thus relates to a crystalline form of N-[1-(5-cyano-pyridin-2-ylmethyl)-1H-pyrazol-3-yl]-2-[4-(1-trifluoromethyl-cyclopropyl)-phenyl]-acetamide according to any one of embodiments 1) to 23) for use as a medicament.

The crystalline solid, especially the essentially pure crystalline solid, of COMPOUND according to any one of embodiments 1) to 23) may be used as single component or as mixture with other crystalline forms or amorphous form of COMPOUND.

25) A further embodiment of the invention relates to pharmaceutical compositions comprising as active ingredient a crystalline form of COMPOUND according to any one of embodiments 1) to 23), and at least one pharmaceutically acceptable carrier material.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the crystalline form of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

26) A further embodiment of the invention relates to a crystalline form of COMPOUND according to any one of embodiments 1) to 23), for use in the manufacture of a pharmaceutical composition, wherein said pharmaceutical composition comprises as active ingredient the COMPOUND, and at least one pharmaceutically acceptable carrier material.

27) A further embodiment of the invention relates to a crystalline form of COMPOUND according to any one of embodiments 1) to 23), for use in the prevention/prophylaxis and/or treatment of a disease or disorder associated with a dysfunction of T-type calcium channels (and notably of a disease or disorder wherein the blockade of the T-type calcium channel subtypes $Ca_v3.1$, $Ca_v3.2$ and/or $Ca_v3.3$ is indicated).

28) A further embodiment of the invention relates to a crystalline form of COMPOUND according to any one of embodiments 1) to 23), for use in the prevention/prophylaxis and/or treatment of a disease or disorder wherein a decrease of burst firing discharges in a neuronal cell by blockade of the T-type calcium channel subtypes $Ca_v3.1$, $Ca_v3.2$ and/or $Ca_v3.3$ is indicated.

The crystalline forms of COMPOUND as defined in any one of embodiments 1) to 23) are useful for the prevention or treatment of diseases or disorders where calcium T channels are involved. Such diseases or disorders where calcium T channels are involved may be defined as including especially:

- epilepsy (notably absence epilepsy, childhood absence and other forms of idiopathic generalized epilepsies, temporal lobe epilepsy);
- sleep disorders and sleep disturbances;
- pain (notably inflammatory pain, neuropathic pain, peripheral pain, chronic pain associated with peripheral axonal injury);
- neurological diseases and disorders (notably essential tremors, Parkinson's disease, schizophrenia, depression, anxiety, psychosis, neurodegenerative disorders, autism, drug addiction);
- cardiovascular diseases and disorders (notably hypertension, cardiac arrhythmias, atrial fibrillation, congenital heart failure, heart block);
- cancer;
- diabetes and diabetic neuropathy; and
- infertility and sexual dysfunction.

Notably such diseases or disorders where calcium T channels are involved refer to epilepsy, neurological disorders, and pain. Preferably such diseases or disorders refer to epilepsy and pain.

The term "pain" preferably refers to inflammatory pain, neuropathic pain, peripheral pain, and chronic pain associated with peripheral axonal injury.

The term "neurological diseases and disorders" preferably refers to essential tremors, Parkinson's disease, schizophrenia, depression, anxiety, psychosis, neurodegenerative disorders, autism and drug addiction.

The term "cardiovascular diseases and disorders" preferably refers to hypertension, cardiac arrhythmias, atrial fibrillation, congenital heart failure and heart block.

29) A further embodiment of the invention relates to a crystalline form of COMPOUND according to any one of embodiments 1) to 23), for use in the prevention/prophylaxis and/or treatment of a disease or disorder selected from epilepsy; sleep disorders; sleep disturbances; pain selected from inflammatory pain, neuropathic pain, peripheral pain, and chronic pain associated with peripheral axonal injury; neurological disorders selected from essential tremors, Parkinson's disease, schizophrenia, depression, anxiety, psychosis, neurodegenerative disorders, autism and drug addiction; cardiovascular disorders selected from hypertension, cardiac arrhythmias, atrial fibrillation, congenital heart failure and heart block; cancer; diabetes; and diabetic neuropathy.

30) A further embodiment of the invention relates to a crystalline form of COMPOUND according to any one of embodiments 1) to 23), for use in the prevention/prophylaxis and/or treatment of a disease or disorder selected from epilepsy; sleep disorders; sleep disturbances; pain selected from inflammatory pain, neuropathic pain, peripheral pain, and chronic pain associated with peripheral axonal injury; essential tremors; Parkinson's disease; schizophrenia; and drug addiction.

31) A further embodiment of the invention relates to a crystalline form of COMPOUND according to any one of embodiments 1) to 23), for use in the prevention/prophylaxis and/or treatment of epilepsy (notably idiopathic generalized epilepsy).

32) A further embodiment of the invention relates to a crystalline form of COMPOUND according to any one of embodiments 1) to 23), for use in the prevention/prophylaxis and/or treatment of focal and/or generalized seizures.

33) A further embodiment of the invention relates to a crystalline form of COMPOUND according to any one of embodiments 1) to 23), for use in the prevention/prophylaxis and/or treatment of focal, tonic, clonic, tonic clonic, absence, myoclonic and/or atonic seizures.

34) A further embodiment of the invention relates to a crystalline form of COMPOUND according to any one of embodiments 1) to 23), for use in the prevention/prophylaxis and/or treatment of tonic clonic, absence, myoclonic and/or atonic seizures.

35) A further embodiment of the invention relates to a crystalline form of COMPOUND according to any one of embodiments 1) to 23), for use in the prevention/prophylaxis and/or treatment of tonic clonic and/or absence seizures.

36) A further embodiment of the invention relates to a crystalline form of COMPOUND according to any one of embodiments 1) to 23), for use in the prevention/prophylaxis and/or treatment of tonic clonic seizures.

37) A further embodiment of the invention relates to a crystalline form of COMPOUND according to any one of embodiments 1) to 23), for use in the prevention/prophylaxis and/or treatment of absence seizures.

The term "epilepsy" describes recurrent unprovoked seizures wherein the term "seizure" refers to an excessive and/or hypersynchronous electrical neuronal activity. Different types of "seizures" are disclosed for example in Berg et al., Epilepsia. 2010; 51(4): 676-685, which reference is herewith incorporated by reference.

For avoidance of any doubt, if a crystalline form of COMPOUND is described as useful for the prevention/prophylaxis and/or treatment of certain diseases, such crystalline form of COMPOUND is likewise suitable for use in the preparation of a medicament for the prevention or treatment of said diseases.

38) A further embodiment of the invention relates to pharmaceutical compositions according to embodiment 25), for use in the prevention/prophylaxis and/or treatment of a disease or disorder associated with a dysfunction of T-type calcium channels (and notably of a disease or disorder wherein the blockade of the T-type calcium channel subtypes $Ca_v3.1$, $Ca_v3.2$ and/or $Ca_v3.3$ is indicated).

39) A further embodiment of the invention relates to pharmaceutical compositions according to embodiment 25), for use in the prevention/prophylaxis and/or treatment of a disease or disorder wherein a decrease of burst firing discharges in a neuronal cell by blockade of the T-type calcium channel subtypes $Ca_v3.1$, $Ca_v3.2$ and/or $Ca_v3.3$ is indicated.

40) A further embodiment of the invention relates to pharmaceutical compositions according to embodiment 25), for use in the prevention/prophylaxis and/or treatment of a disease or disorder selected from epilepsy; sleep disorders; sleep disturbances; pain selected from inflammatory pain, neuropathic pain, peripheral pain, and chronic pain associated with peripheral axonal injury; neurological disorders selected from essential tremors, Parkinson's disease, schizophrenia, depression, anxiety, psychosis, neurodegenerative disorders, autism and drug addiction; cardiovascular disorders selected from hypertension, cardiac arrhythmias, atrial fibrillation, congenital heart failure and heart block; cancer; diabetes; and diabetic neuropathy.

41) A further embodiment of the invention relates to pharmaceutical compositions according to embodiment 25), for use in the prevention/prophylaxis and/or treatment of a disease or disorder selected from epilepsy; sleep disorders; sleep disturbances; pain selected from inflammatory pain, neuropathic pain, peripheral pain, and chronic pain associated with peripheral axonal injury; essential tremors; Parkinson's disease; schizophrenia; and drug addiction.

42) A further embodiment of the invention relates to pharmaceutical compositions according to embodiment 25), for use in the prevention/prophylaxis and/or treatment of epilepsy (notably idiopathic generalized epilepsy).

43) A further embodiment of the invention relates to pharmaceutical compositions according to embodiment 25), for use in the prevention/prophylaxis and/or treatment of focal and/or generalized seizures.

44) A further embodiment of the invention relates to pharmaceutical compositions according to embodiment 25), for use in the prevention/prophylaxis and/or treatment of focal, tonic, clonic, tonic clonic, absence, myoclonic and/or atonic seizures.

45) A further embodiment of the invention relates to pharmaceutical compositions according to embodiment 25), for use in the prevention/prophylaxis and/or treatment of tonic clonic, absence, myoclonic and/or atonic seizures.

46) A further embodiment of the invention relates to pharmaceutical compositions according to embodiment 25), for use in the prevention/prophylaxis and/or treatment of tonic clonic and/or absence seizures.

47) A further embodiment of the invention relates to pharmaceutical compositions according to embodiment 25), for use in the prevention/prophylaxis and/or treatment of tonic clonic seizures.

48) A further embodiment of the invention relates to pharmaceutical compositions according to embodiment 25), for use in the prevention/prophylaxis and/or treatment of absence seizures.

The present invention also relates to a method for the prevention/prophylaxis and/or treatment of a disease or disorder mentioned herein, comprising administering to a subject a pharmaceutically active amount of a crystalline form of COMPOUND according to any one of embodiments 1) to 23), or of a pharmaceutical composition according to embodiment 25).

EXPERIMENTAL PROCEDURES

Abbreviations (as Used Hereinbefore or Hereinafter)

DIPEA Diisopropylethylamine
DSC Differential scanning calorimetry
eq Equivalent(s)
EtOAc Ethyl acetate
Fig Figure
h Hour(s)
$^1$H-NMR Nuclear magnetic resonance of the proton
HATU O-(7-Azabenzotriazol-1-yl)-N,N,N',N'-tetramethyluronium hexafluorophosphate
HPLC High performance liquid chromatography
LC-MS Liquid chromatography—Mass Spectrometry
min Minute(s)
MS Mass spectrometry
NMR Nuclear magnetic resonance
Ph. Eur. European Pharmacopeia
RT Room temperature
sat. Saturated
TFA trifluoroacetic acid
$t_R$ Retention time
vol. L solvent per kg starting material
XRPD X-ray powder diffraction All solvents and reagents are used as obtained from commercial sources unless otherwise indicated.

Temperatures are indicated in degrees Celsius (° C.). Unless otherwise indicated, the reactions take place at room temperature (RT).

Analytical LC-MS conditions as used in the Examples below:

Column: Zorbax SB-Aq, 3.5 μm, 4.6×50 mm, heated to 40.0° C.; gradient: 5% $CH_3CN$/95% $H_2O$ with 0.04% TFA to 95% $CH_3CN$/5% $H_2O$ with 0.04% TFA over 1.0 min, flow 4.5 mL/min; MS: Thermo MSQ Plus in ESI+ ionisation mode.

X-Ray Powder Diffraction Analysis (XRPD)

X-ray powder diffraction patterns were collected on a Bruker D8 Advance X-ray diffractometer equipped with a Lynxeye detector operated with CuKα-radiation in reflection mode (coupled two Theta/Theta). Typically, the X-ray tube was run at of 40 kV/40 mA. A step size of 0.02° (2θ) and a step time of 76.8 sec over a scanning range of 3-50° in 2θ were applied. The divergence slits were set to fixed 0.3°. Powders were slightly pressed into a silicon single crystal sample holder with depth of 0.5 mm and samples were rotated in their own plane during the measurement. Diffraction data are reported without application of Kα2 stripping. The accuracy of the 2θ values as provided herein is in the range of +/−0.1-0.2° as it is generally the case for conventionally recorded X-ray powder diffraction patterns.

Gravimetric Vapour Sorption (GVS) Analysis

Measurements were performed on an IGASORP Model HAS-036-080 moisture sorption instrument (Hiden Isochema, Warrington, UK) operated in stepping mode at 25° C. The sample was allowed to equilibrate at the starting relative humidity (RH) before starting a pre-defined humidity program in steps of 5% ΔRH and with a maximal equilibration time of 24 hours per step. About 20 to 30 mg of each sample was used.

Differential Scanning Calorimetry (DSC)

DSC data were collected on a Mettler Toledo STARe System (DSC822e module, measuring cell with ceramic sensor and STAR software version 13.00) equipped with a 34 position auto-sampler. The instrument was calibrated for energy and temperature using certified indium. Typically 2 mg of each sample, in an automatically pierced 40 μL Mettler aluminium pan, was heated at 10° C. $min^{-1}$, unless stated otherwise, from −20° C. to 280° C. A nitrogen purge at 20 ml $min^{-1}$ was maintained over the sample. Peak temperatures are reported for melting points.

I-Chemistry

The starting materials 6-((3-Amino-1H-pyrazol-1-yl)methyl)nicotinonitrile and 2-(4-(1-(trifluoromethyl)cyclopropyl)phenyl)acetic acid can be prepared according to the procedures given in WO 2015/186056, page 54, lines 24 to 27 and page 109, lines 27 to 30, respectively.

II. Preparation of Crystalline Forms of COMPOUND

Example 1: Preparation and Characterization of COMPOUND in Crystalline Form 1

To a solution of 2-(4-(1-(trifluoromethyl)cyclopropyl)phenyl)acetic acid (41 mmol, 1.0 eq.) in acetonitrile (280 mL) was added DIPEA (90 mmol, 2.2 eq.) and HATU (43 mmol, 1.05 eq.), respectively, and the solution was stirred at RT under nitrogen atmosphere for 5 min. 6-((3-amino-1H-pyrazol-1-yl)methyl)nicotinonitrile (43 mmol, 1.05 eq.) was added, the solution was stirred at RT for about 18 h and the solvent was removed under vacuo. The residue was dissolved in EtOAc and washed successively with aqueous hydrochloric acid (0.1 M), aqueous sat. $NaHCO_3$ solution and water. The organic layer was dried over $Na_2SO_4$ and concentrated in vacuo. The residue was purified by flash chromatography on silica gel (gradient: n-heptane to EtOAc). Crystallization: toluene (70 mL) was added to the obtained solid (14 g) and the suspension was heated to reflux until complete dissolution. The solution was allowed to reach RT within about 90 min. After further cooling to 0° C., the suspension was filtered and the residue was washed with n-pentane and dried in vacuo to give a crystalline solid (10 g) in crystalline form 1.

TABLE 1

Characterisation data for COMPOUND in crystalline form 1

| Technique | Data Summary | Remarks |
|---|---|---|
| XRPD | Crystalline | see FIG. 1 |
| 1H-NMR | Consistent | |
| LC-MS | $t_R$ = 0.87 min; $[M + H]^+$ = 426.1 | |
| DSC | Melt endotherm with melting point at T = 147 ± 2° C. | |
| Moisture sorption at 25° C. (GVS) | COMPOUND in crystalline form 1 is not hygroscopic according to Ph. Eur. | |

Example 2: Preparation and Characterization of COMPOUND in Crystalline Form 2

COMPOUND in crystalline form 1 (5 mg) was dissolved in either acetone (40 μL) or butanone (50 μL) in a 4 mL glass vial and the solvent was allowed to evaporate at ambient conditions from the open vial to give from both solvents a crystalline solid in crystalline form 2.

TABLE 2

Characterisation data for COMPOUND in crystalline form 2

| Technique | Data Summary | Remarks |
|---|---|---|
| XRPD | Crystalline | see FIG. 2 |
| 1H-NMR | Consistent | |

The invention claimed is:

1. A crystalline form of N-[1-(5-cyano-pyridin-2-ylmethyl)-1H-pyrazol-3-yl]-2-[4-(1-trifluoromethyl-cyclopropyl)-phenyl]-acetamide, characterized by:
   a. the presence of peaks in the X-ray powder diffraction diagram at the following angles of refraction 2θ: 4.7°, 14.1°, and 20.1°, or b. the presence of peaks in the X-ray powder diffraction diagram at the following angles of refraction 2θ: 12.8°, 18.0°, and 18.3°.

2. A crystalline form of N-[1-(5-cyano-pyridin-2-ylmethyl)-1H-pyrazol-3-yl]-2-[4-(1-trifluoromethyl-cyclopropyl)-phenyl]-acetamide according to claim 1, characterized by
   a. the presence of peaks in the X-ray powder diffraction diagram at the following angles of refraction 2θ: 4.7°, 9.3°, 14.1°, 20.1°, and 24.7°; or
   b. the presence of peaks in the X-ray powder diffraction diagram at the following angles of refraction 2θ: 12.4°, 12.8°, 15.7°, 18.0°, and 18.3°.

3. A crystalline form of N-[1-(5-cyano-pyridin-2-ylmethyl)-1H-pyrazol-3-yl]-2-[4-(1-trifluoromethyl-cyclopropyl)-phenyl]-acetamide according to claim 1, characterized by the presence of peaks in the X-ray powder diffraction diagram at the following angles of refraction 2θ: 4.7°, 14.1°, and 20.1°.

4. A crystalline form of N-[1-(5-cyano-pyridin-2-ylmethyl)-1H-pyrazol-3-yl]-2-[4-(1-trifluoromethyl-cyclopropyl)-phenyl]-acetamide according to claim 1, characterized by the presence of peaks in the X-ray powder diffraction diagram at the following angles of refraction 2θ: 4.7°, 9.3°, 12.0°, 14.1°, 16.3°, 18.4°, 20.1°, 21.8°, 24.7°, and 28.6°.

5. A crystalline form of N-[1-(5-cyano-pyridin-2-ylmethyl)-1H-pyrazol-3-yl]-2-[4-(1-trifluoromethyl-cyclopropyl)-phenyl]-acetamide according to claim 1, characterized by the presence of peaks in the X-ray powder diffraction diagram at the following angles of refraction 2θ: 12.8°, 18.0°, and 18.3°.

6. A crystalline form of N-[1-(5-cyano-pyridin-2-ylmethyl)-1H-pyrazol-3-yl]-2-[4-(1-trifluoromethyl-cyclopropyl)-phenyl]-acetamide according to claim 1, characterized by the presence of peaks in the X-ray powder diffraction diagram at the following angles of refraction 2θ: 10.9°, 12.4°, 12.8°, 13.2°, 15.7°, 16.3°, 18.0°, 18.3°, 21.1°, and 29.3°.

7. A crystalline form of N-[1-(5-cyano-pyridin-2-ylmethyl)-1H-pyrazol-3-yl]-2-[4-(1-trifluoromethyl-cyclopropyl)-phenyl]-acetamide, characterized by:
   a. the presence of peaks in the X-ray powder diffraction diagram at the following angles of refraction 2θ: 4.7°, 14.1°, and 20.1°, or
   b. obtainable by:
   a. heating a suspension comprising N-[1-(5-cyano-pyridin-2-ylmethyl)-1H-pyrazol-3-yl]-2-[4-(1-trifluoromethyl-cyclopropyl)-phenyl]-acetamide in about 5 vol. toluene at reflux until dissolution;
   b. cooling of the solution to about 25° C. within 1 to 5 hours;
   c. cooling to 0° C.; and
   d. isolating of the obtained solid residue.

8. A pharmaceutical composition comprising as active ingredient a crystalline form of N-[1-(5-cyano-pyridin-2-ylmethyl)-1H-pyrazol-3-yl]-2-[4-(1-trifluoromethyl-cyclopropyl)-phenyl]-acetamide according to claim 1, and at least one pharmaceutically acceptable carrier.

9. A method for treating a disease or disorder selected from epilepsy; sleep disorders; sleep disturbances; pain selected from inflammatory pain, neuropathic pain, peripheral pain, and chronic pain associated with peripheral axonal injury; neurological disorders selected from essential tremors, Parkinson's disease, schizophrenia, depression, anxiety, psychosis, neurodegenerative disorders, autism and drug addiction; cardiovascular disorders selected from hypertension, cardiac arrhythmias, atrial fibrillation, congenital heart failure and heart block; cancer; diabetes; and diabetic neuropathy, the method comprising administering a pharmaceutically effective amount of the crystalline form of N-[1-(5-cyano-pyridin-2-ylmethyl)-1H-pyrazol-3-yl]-2-[4-(1-trifluoromethyl-cyclopropyl)-phenyl]-acetamide according to claim 1 to a subject in need thereof.

10. A method for treating epilepsy, the method comprising administering a pharmaceutically effective amount of the crystalline form of N-[1-(5-cyano-pyridin-2-ylmethyl)-1H-pyrazol-3-yl]-2-[4-(1-trifluoromethyl-cyclopropyl)-phenyl]-acetamide according to claim 1 to a subject in need thereof.

11. The method according to claim 9, wherein the crystalline form of N-[1-(5-cyano-pyridin-2-ylmethyl)-1H-pyrazol-3-yl]-2-[4-(1-trifluoromethyl-cyclopropyl)-phenyl]-acetamide is characterized by
   a. the presence of peaks in the X-ray powder diffraction diagram at the following angles of refraction 2θ: 4.7°, 9.3°, 14.1°, 20.1°, and 24.7°; or b. the presence of peaks in the X-ray powder diffraction diagram at the following angles of refraction 2θ: 12.4°, 12.8°, 15.7°, 18.0°, and 18.3°.

12. The method according to claim 10, wherein the crystalline form of N-[1-(5-cyano-pyridin-2-ylmethyl)-1H-pyrazol-3-yl]-2-[4-(1-trifluoromethyl-cyclopropyl)-phenyl]-acetamide is characterized by a. the presence of peaks in the X-ray powder diffraction diagram at the following angles of refraction 2θ: 4.7°, 9.3°, 14.1°, 20.1°, and 24.7°; or b. the presence of peaks in the X-ray powder diffraction diagram at the following angles of refraction 2θ: 12.4°, 12.8°, 15.7°, 18.0°, and 18.3°.

\* \* \* \* \*

UNITED STATES PATENT AND TRADEMARK OFFICE
CERTIFICATE OF CORRECTION

PATENT NO. : 11,059,803 B2
APPLICATION NO. : 16/628618
DATED : July 13, 2021
INVENTOR(S) : Bibia Heidmann and Markus Von Raumer It is certified that error appears in the above-identified patent and that said Letters Patent is hereby corrected as shown below:

In the Claims

Claim 7, Column 12, Lines 20-26:
"A crystalline form of N-[1-(5-cyano-pyridin-2-ylmethyl)-1H-pyrazol-3-yl]-2-[4-(1-trifluoromethyl-cyclopropyl)-phenyl]-acetamide, characterized by:
a. the presence of peaks in the X-ray powder diffraction diagram at the following angles of refraction $2\theta$: 4.7°, 14.1°, and 20.1°, or
b. obtainable by:"
Should read:
-- A crystalline form of N-[1-(5-cyano-pyridin-2-ylmethyl)-1H-pyrazol-3-yl]-2-[4-(1-trifluoromethyl-cyclopro-pyl)-phenyl]-acetamide, characterized by the presence of peaks in the X-ray powder diffraction diagram at the following angles of refraction $2\theta$: 4.7°, 14.1°, and 20.1°, obtainable by: --

Signed and Sealed this
Nineteenth Day of July, 2022

Katherine Kelly Vidal
*Director of the United States Patent and Trademark Office*